(12) United States Patent
Cisneros

(10) Patent No.: US 6,878,034 B1
(45) Date of Patent: Apr. 12, 2005

(54) BREAST PROTECTION DEVICE FOR A NURSING MOTHER

(76) Inventor: Marika L. Cisneros, P.O. Box 6183, Austin, TX (US) 78762-6183

(*) Notice: Subject to any disclaimer, the term of this patent is extended or adjusted under 35 U.S.C. 154(b) by 0 days.

(21) Appl. No.: 10/788,852

(22) Filed: Mar. 1, 2004

(51) Int. Cl.$^7$ ................................................. A41C 3/00
(52) U.S. Cl. ........................ 450/57; 450/36; 604/385.07
(58) Field of Search ...................... 450/36–39, 54–57, 450/81; 604/385.01, 385.23, 385.03, 387–390, 385.07, 358, 363–375; 128/890; 2/267, 455, 463–465; 602/60, 61; 623/7, 8; 424/400–402, 420, 443–448, 78.02–78.03

(56) References Cited

U.S. PATENT DOCUMENTS

| | | | | |
|---|---|---|---|---|
| 2,627,606 A | * | 2/1953 | De Grandis | 450/57 |
| 2,891,544 A | * | 6/1959 | London | 604/379 |
| 3,513,852 A | * | 5/1970 | Seidl | 450/36 |
| 4,674,510 A | * | 6/1987 | Sneider | 450/57 |
| 5,281,186 A | * | 1/1994 | Buckley et al. | 450/31 |
| 5,683,286 A | * | 11/1997 | Kielland | 450/37 |
| 5,806,103 A | * | 9/1998 | McCracken et al. | 2/455 |
| 6,036,577 A | * | 3/2000 | Coburn | 450/57 |
| 6,039,629 A | * | 3/2000 | Mitchell | 450/57 |
| 6,338,665 B1 | * | 1/2002 | Dawson et al. | 450/57 |
| 6,390,886 B1 | * | 5/2002 | Roberts | 450/37 |
| 6,695,678 B1 | * | 2/2004 | Foley et al. | 450/57 |

* cited by examiner

Primary Examiner—Gloria M. Hale

(57) ABSTRACT

A breast protection device for a nursing mother for providing absorbent and skin irritant-less material for the breast of a nursing mother. The breast protection device for a nursing mother includes a convexo-concave member being adapted to fit over a breast of a nursing mother; and also includes a pad member being attached to a concave side of the convexo-concave member; and further includes an assembly of covering the pad member; and further includes a fastening member being attached to the convex side of the convexo-concave member for attaching to a bra of the nursing mother.

6 Claims, 4 Drawing Sheets

US 6,878,034 B1

BREAST PROTECTION DEVICE FOR A NURSING MOTHER

BACKGROUND OF THE INVENTION

1. Field of the Invention

The present invention relates to breast protectors and more particularly pertains to a new breast protection device for a nursing mother for providing absorbent and skin irritant-less material for the breast of a nursing mother.

2. Description of the Prior Art

The use of breast protectors is known in the prior art. More specifically, breast protectors heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 6,074,272; U.S. Pat. No. 4,125,114; U.S. Pat. No. 5,149,336; U.S. Pat. No. 4,748,976; U.S. Pat. No. 6,039,629; and U.S. Pat. No. Des. 246,729.

While these devices fulfill their respective, particular objectives and requirements, the aforementioned patents do not disclose a new breast protection device for a nursing mother. The prior art includes cup-shaped pads being placed over he breasts of nursing mothers.

SUMMARY OF THE INVENTION

The general purpose of the present invention, which will be described subsequently in greater detail, is to provide a new breast protection device for a nursing mother which has many of the advantages of the breast protectors mentioned heretofore and many novel features that result in a new breast protection device for a nursing mother which is not anticipated, rendered obvious, suggested, or even implied by any of the prior art breast protectors, either alone or in any combination thereof. The present invention includes a convexo-concave member being adapted to fit over a breast of a nursing mother; and also includes a pad member being attached to a concave side of the convexo-concave member; and further includes an assembly of covering the pad member; and further includes a fastening member being attached to the convex side of the convexo-concave member for attaching to a bra of the nursing mother. None of the prior art includes the combination of the elements of the present invention.

There has thus been outlined, rather broadly, the more important features of the breast protection device for a nursing mother in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new breast protection device for a nursing mother which has many of the advantages of the breast protectors mentioned heretofore and many novel features that result in a new breast protection device for a nursing mother which is not anticipated, rendered obvious, suggested, or even implied by any of the prior art breast protectors, either alone or in any combination thereof.

Still another object of the present invention is to provide a new breast protection device for a nursing mother for providing absorbent and skin irritant-less material for the breast of a nursing mother.

Still yet another object of the present invention is to provide a new breast protection device for a nursing mother that is easy and convenient to use.

Even still another object of the present invention is to provide a new breast protection device for a nursing mother that removes the moisture away from the nipple of the nursing mother and also prevents shifting of the breast protection device which otherwise would cause irritation to the breast of the nursing mother.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
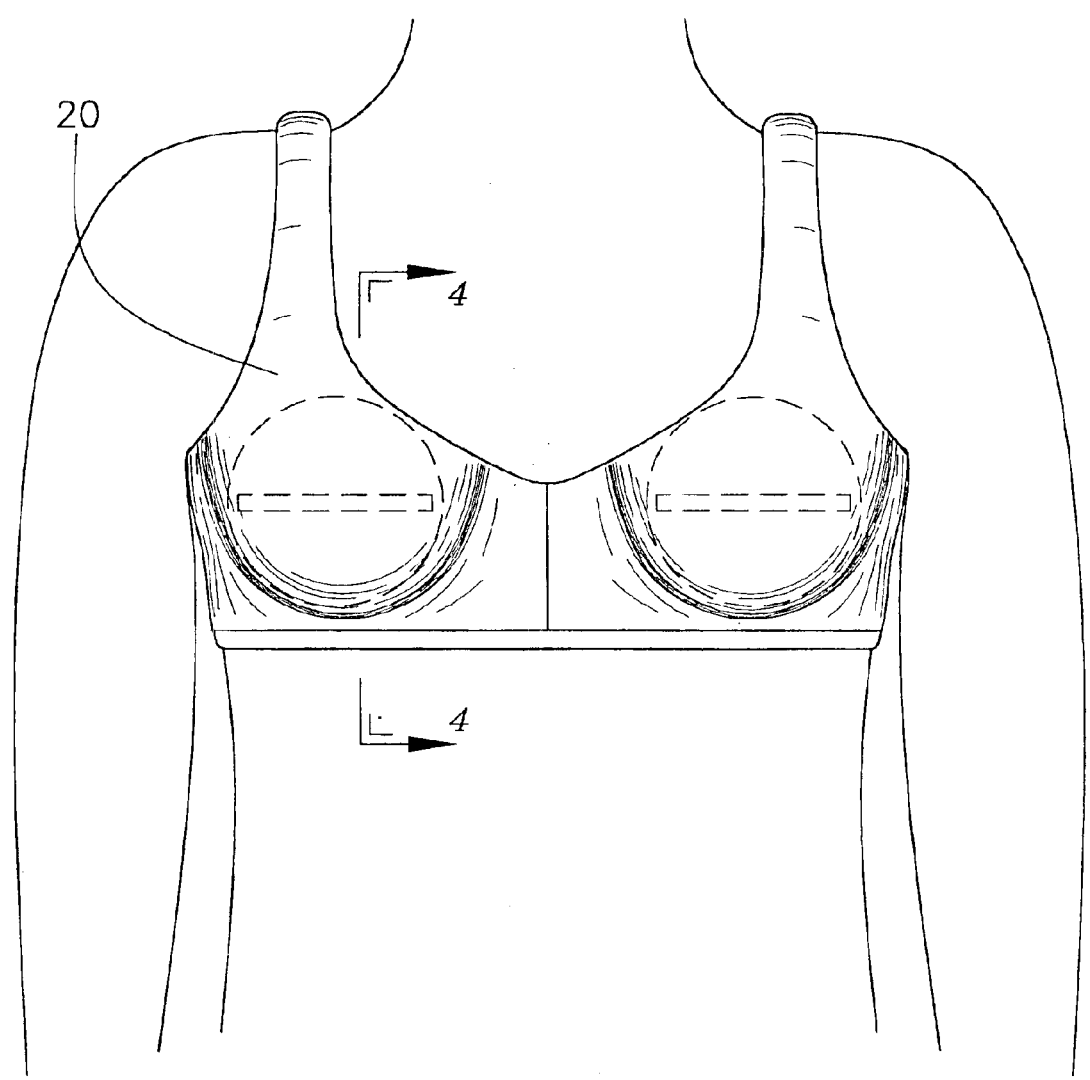
FIG. 1 is a front elevational view of a new breast protection device for a nursing mother according to the present invention.
Figure 2:
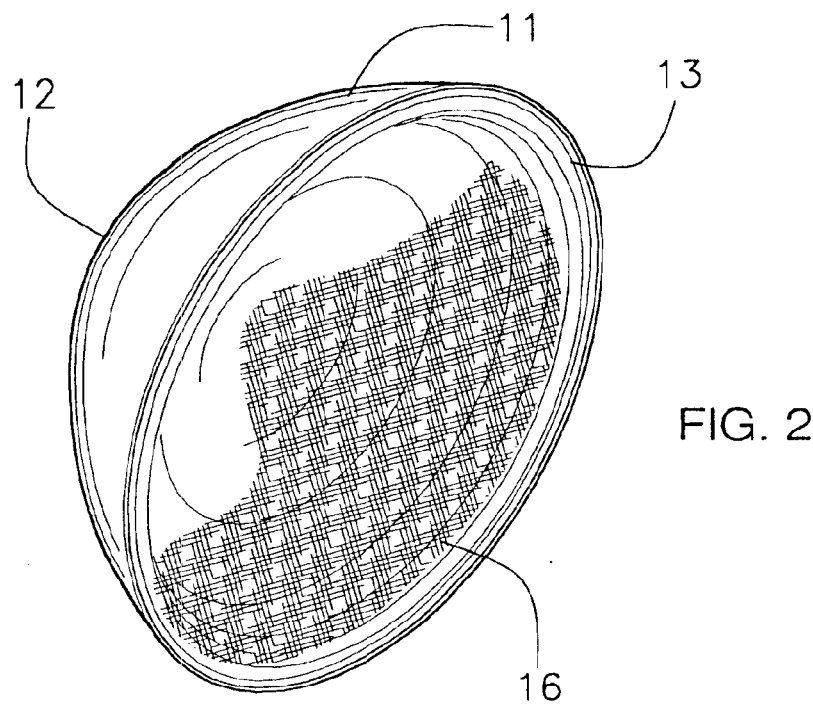
FIG. 2 is a rear perspective view of the present invention.
Figure 3:
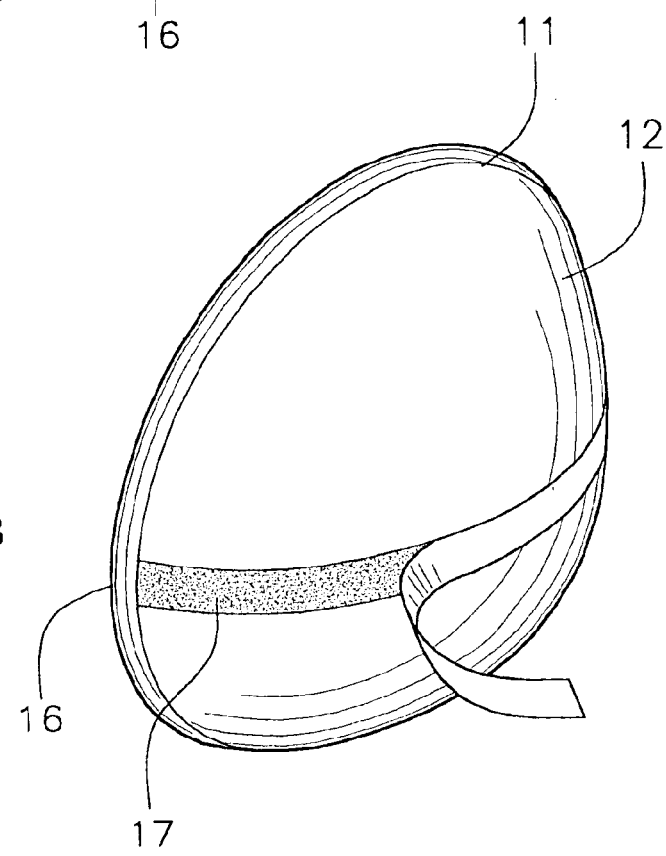
FIG. 3 is a front perspective view of the present invention.
Figure 4:
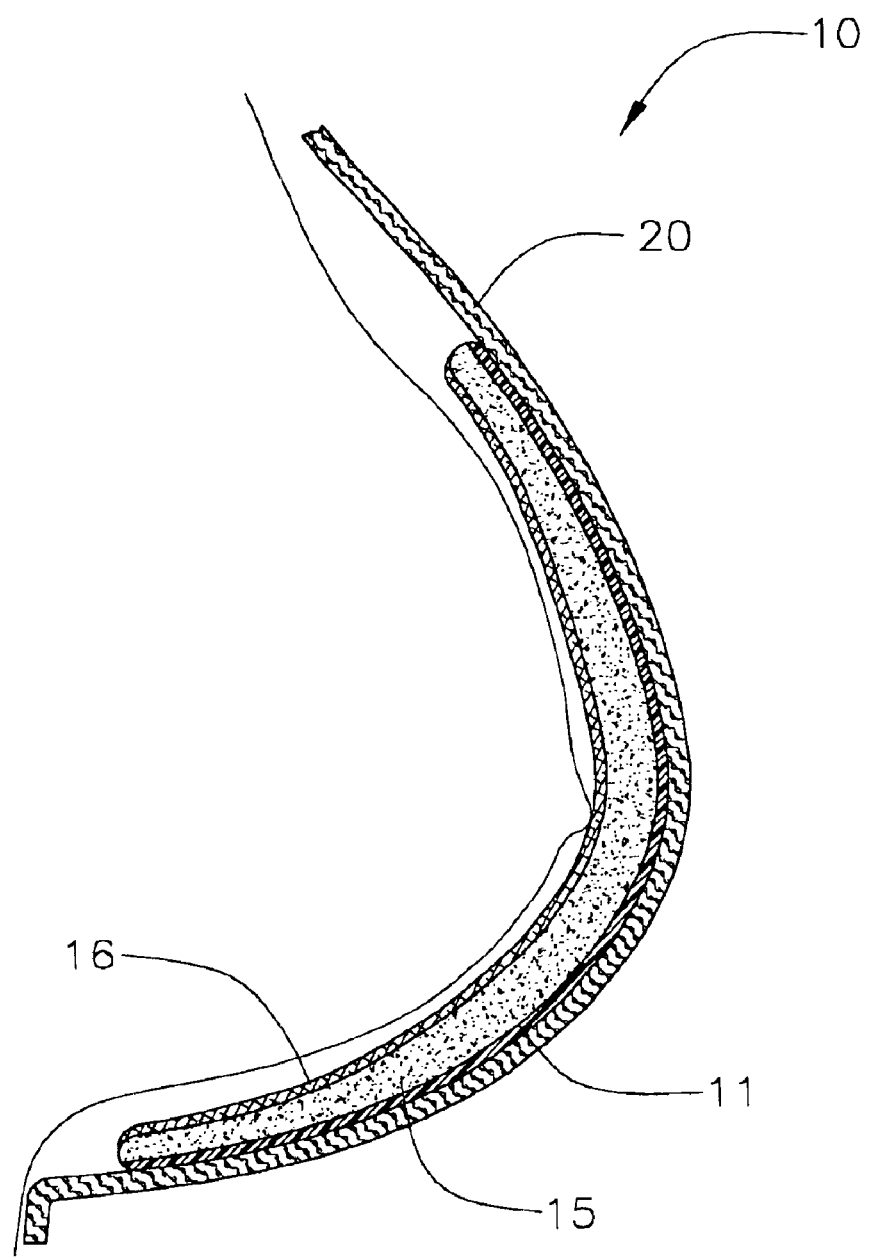
FIG. 4 is a cross-sectional view of the present invention.
Figure 5:
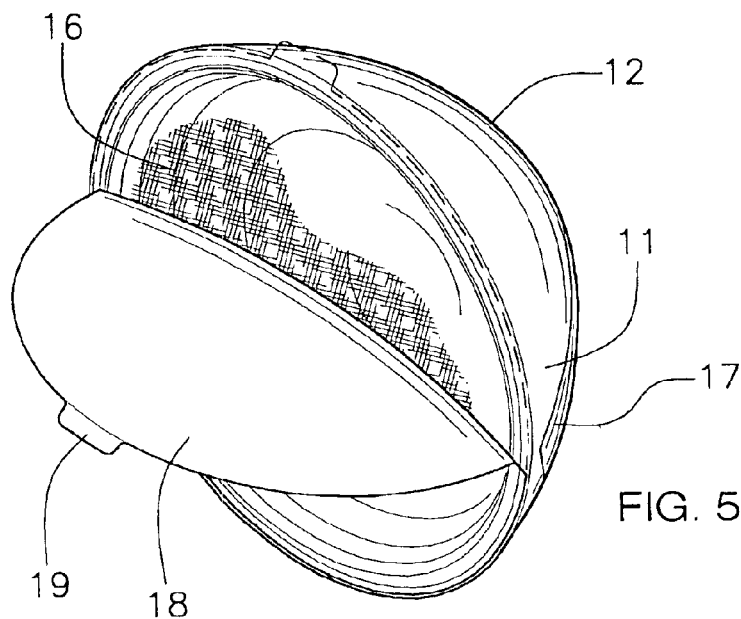
FIG. 5 is a rear perspective view of a second embodiment of the present invention.
Figure 6:
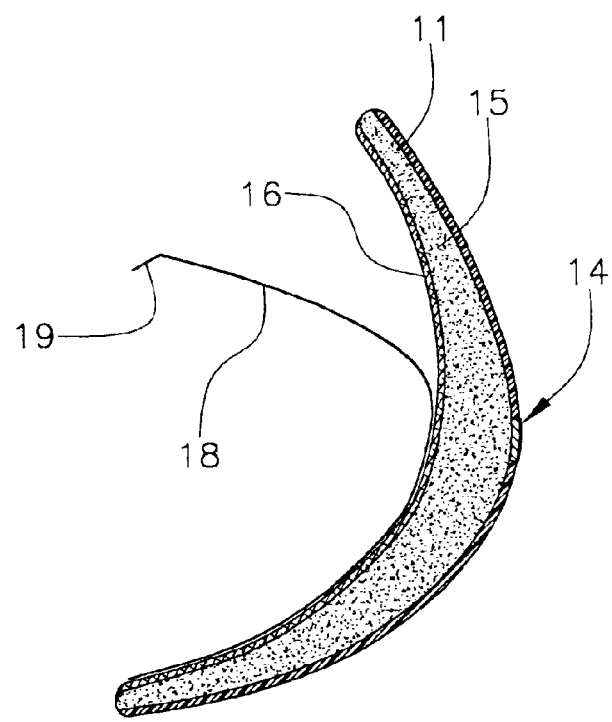
FIG. 6 is a cross-sectional view of the second embodiment of the present invention.

With reference now to the drawings, and in particular to FIGS. 1 through 6 thereof, a new breast protection device for a nursing mother embodying the principles and concepts of the present invention and generally designated by the reference numeral will be described.

As best illustrated in FIGS. 1 through 6, the breast protection device for a nursing mother 10 generally comprises a convexo-concave member 11 being adapted to fit over a breast of a nursing mother. The convexo-concave member 11 is a rigid shell made of a plastic material which is adapted to fit about and not rest against the breast 21 of the nursing mother. The convexo-concave member 11 has an elongate slot 14 being disposed in a convex side 12 thereof. A pad member 15 is securely attached to a concave side 13 of the convexo-concave member 11 and is made of absorbent cotton material.

A means of covering the pad member 15 includes a woven sheet of material 16 overlaying the pad member 15. The woven sheet of material 16 is made of woven micro-fibers being coated with Lanolin to allow moisture to seep through to the pad member 15 and to keep the moisture away from the breast of the nursing mother. As a second embodiment, the means of covering the pad member 15 also includes a cover member 18 being removably disposed over the concave side 13 of the convexo-concave member 11 and having a pull tab 19 being integrally attached to an edge thereof for pulling the cover member 18 off the concave side 13 of the convexo-concave member 11.

A fastening member 17 is securely attached to the convex side 12 of the convexo-concave member 11 for attaching the convexo-concave member 11 to the bra 20 of the nursing mother. The fastening member 17 is a strip of adhesive tape being securely disposed in the elongate slot 14 and being generally flush with the convex side 12 of the convexo-concave member 11 and being adhereable to the bra 20 of the nursing mother.

In use, once the mother finishes breast feeding the child, she would place the convex side 12 of the convexo-concave member 11 against the inner side of the cup of the bra 20 so that the strip of adhesive tape 17 adheres to the bra 20 to prevent movement of the convexo-concave member 11 about the breast of the mother. Any leakage from the breast would seep through the woven sheet of material 16 and be absorbed in the pad member 15.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the breast protection device for a nursing mother. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A breast protection device for a nursing mother comprising:

a convexo-concave member being adapted to fit over a breast of a nursing mother, said convexo-concave member being a rigid shell made of a plastic material which fits about and not rest against the breast of the nursing mother;

a pad member being attached to a concave side of said convexo-concave member;

a means of covering said pad member; and a fastening member being attached to said convex side of said convexo-concave member for attaching said convexo-concave member to a bra of the nursing mother.

2. The breast protection device for a nursing mother as described in claim 1, wherein said convexo-concave member has an elongate slot being disposed in a convex side thereof.

3. The breast protection device for a nursing mother as described in claim 2, wherein said pad member is made of absorbent cotton material.

4. The breast protection device for a nursing mother as described in claim 3, wherein said means of covering said pad member includes a woven sheet of material overlaying said pad member, said woven sheet of material being made of woven micro-fibers and being coated with Lanolin to allow moisture to seep through to said pad member and to keep moisture away from the breast of the nursing mother.

5. The breast protection device for a nursing mother as described in claim 4, wherein said fastening member is a strip of adhesive tape being disposed in said elongate slot and being generally flush with said convex side of said convexo-concave member and being adhereable to the bra of the nursing mother.

6. The breast protection device for a nursing mother as described in claim 5, wherein said means of covering said pad member also includes a cover member being removably disposed over said concave side of said convexo-concave member and having a pull tab being attached to an edge thereof for pulling said cover member off said concave side of said convexo-concave member.

\* \* \* \* \*